(12) United States Patent (10) Patent No.: US 7,490,981 B2
Petrovic (45) Date of Patent: Feb. 17, 2009

(54) METHOD FOR DETERMINING THERMAL EFFUSIVITY AND/OR THERMAL CONDUCTIVITY OF SHEET MATERIAL

(75) Inventor: Ivan Petrovic, Princeton, NJ (US)

(73) Assignee: BASF Catalysts LLC, Florham Park, NJ (US)

( * ) Notice: Subject to any disclaimer, the term of this patent is extended or adjusted under 35 U.S.C. 154(b) by 254 days.

(21) Appl. No.: 11/464,272

(22) Filed: Aug. 14, 2006

(65) Prior Publication Data

US 2007/0127543 A1 Jun. 7, 2007

Related U.S. Application Data

(60) Provisional application No. 60/741,302, filed on Dec. 1, 2005.

(51) Int. Cl.
*G01N 25/18* (2006.01)
(52) U.S. Cl. .......................................... 374/44; 374/43
(58) Field of Classification Search .............. 374/43–44
See application file for complete search history.

(56) References Cited

U.S. PATENT DOCUMENTS

| | | | | |
|---|---|---|---|---|
| 5,005,985 A | * | 4/1991 | Piorkowska-Galeska et al. ......................... | 374/44 |
| 5,407,891 A | | 4/1995 | Matsushita et al. | |
| 5,441,343 A | * | 8/1995 | Pylkki et al. ................. | 374/137 |
| 5,688,049 A | * | 11/1997 | Govorkov ..................... | 374/44 |
| 5,786,839 A | | 7/1998 | Itoh | |
| 6,095,679 A | * | 8/2000 | Hammiche et al. ............ | 374/43 |
| 6,331,075 B1 | * | 12/2001 | Amer et al. .................... | 374/44 |
| 6,566,301 B2 | | 5/2003 | Mathiaparanam et al. | |
| 6,676,287 B1 | | 1/2004 | Mathis | |
| 6,991,366 B2 | * | 1/2006 | Naka et al. .................... | 374/44 |
| 7,182,510 B2 | * | 2/2007 | Cahill .......................... | 374/44 |
| 2002/0080850 A1 | * | 6/2002 | Baba ............................ | 374/43 |
| 2002/0131476 A1 | * | 9/2002 | Baba et al. ................... | 374/161 |
| 2003/0222935 A1 | * | 12/2003 | Yabuta ......................... | 347/19 |
| 2005/0002435 A1 | * | 1/2005 | Hashimoto et al. ............ | 374/43 |
| 2005/0002436 A1 | * | 1/2005 | Taketoshi et al. ............. | 374/43 |
| 2006/0039443 A1 | * | 2/2006 | Watanabe et al. ............. | 374/44 |
| 2006/0122059 A1 | * | 6/2006 | Mathur et al. ................ | 503/200 |
| 2006/0222043 A1 | * | 10/2006 | Cahill .......................... | 374/44 |

* cited by examiner

*Primary Examiner*—Edward Lefkowitz
*Assistant Examiner*—Bret Adams
(74) *Attorney, Agent, or Firm*—Bernard Lau; Greg Turocy

(57) ABSTRACT

Disclosed is a method for determining thermal effusivity and/or thermal conductivity of a sheet material or of coated substrate having a thickness of less than about 100 μm. The method contains providing a sample by layering more than 2 sheet materials or coated substrates and measuring thermal effusivity and/or thermal conductivity of the sample by a thermal effusivity probe and/or thermal conductivity probe.

20 Claims, 2 Drawing Sheets

METHOD FOR DETERMINING THERMAL EFFUSIVITY AND/OR THERMAL CONDUCTIVITY OF SHEET MATERIAL

RELATED APPLICATION

This application claims priority to U.S. Provisional Patent Application 60/741,302 filed on Dec. 1, 2005, which is hereby incorporated by reference.

TECHNICAL FIELD

The subject invention generally relates to a method for determining thermal effusivity and/or thermal conductivity of a sheet material or of a coated substrate.

BACKGROUND

The thermal properties of materials can be characterized by a number of characteristics, such as thermal conductivity and thermal effusivity. Thermal conductivity is a measure of the ability of a material to conduct heat (W/mK). Thermal effusivity is defined as the square root of the product of thermal conductivity (W/mK) times the density ($kg/m^3$) times heat capacity (J/kgK). Thermal effusivity is a heat transfer property that can indicate the interfacial temperature when two semi-infinite objects at different temperatures touch.

Thermal effusivity and thermal conductivity provide a quantitative measure of the thermal impedance of a region of material and a tool to test consistent quality on a film product. Thermal properties of sheet material usually depend on how the material is processed among other factors, and information related to the thermal properties can be helpful in developing new products. However, there are difficulties in measuring the thermal effusivity and/or thermal conductivity of very thin layers of sheet materials, especially very thin coatings on much thicker substrates.

SUMMARY

The following presents a simplified summary in order to provide a basic understanding of some aspects of the invention. This summary is not an extensive overview of the invention. It is intended to neither identify key or critical elements of the invention nor delineate the scope of the invention. Rather, the sole purpose of this summary is to present some concepts of the invention in a simplified form as a prelude to the more detailed description that is presented hereinafter.

The subject invention provides methods for determining thermal effusivity and/or thermal conductivity of a thin sheet material. The subject invention also provides methods for determining thermal effusivity and/or thermal conductivity of a coated substrate. The methods involve providing a sample by layering 2 or more sheet materials or coated substrates; placing the sample onto a thermal effusivity probe/sensor and/or thermal conductivity probe/sensor; and measuring thermal effusivity and/or thermal conductivity of the sample by the thermal effusivity probe/sensor and/or thermal conductivity probe/sensor.

To the accomplishment of the foregoing and related ends, the invention comprises the features hereinafter fully described and particularly pointed out in the claims. The following description and the annexed drawings set forth in detail certain illustrative aspects and implementations of the invention. These are indicative, however, of but a few of the various ways in which the principles of the invention may be employed. Other objects, advantages and novel features of the invention will become apparent from the following detailed description of the invention when considered in conjunction with the drawings.

DETAILED DESCRIPTION

Figure 1:
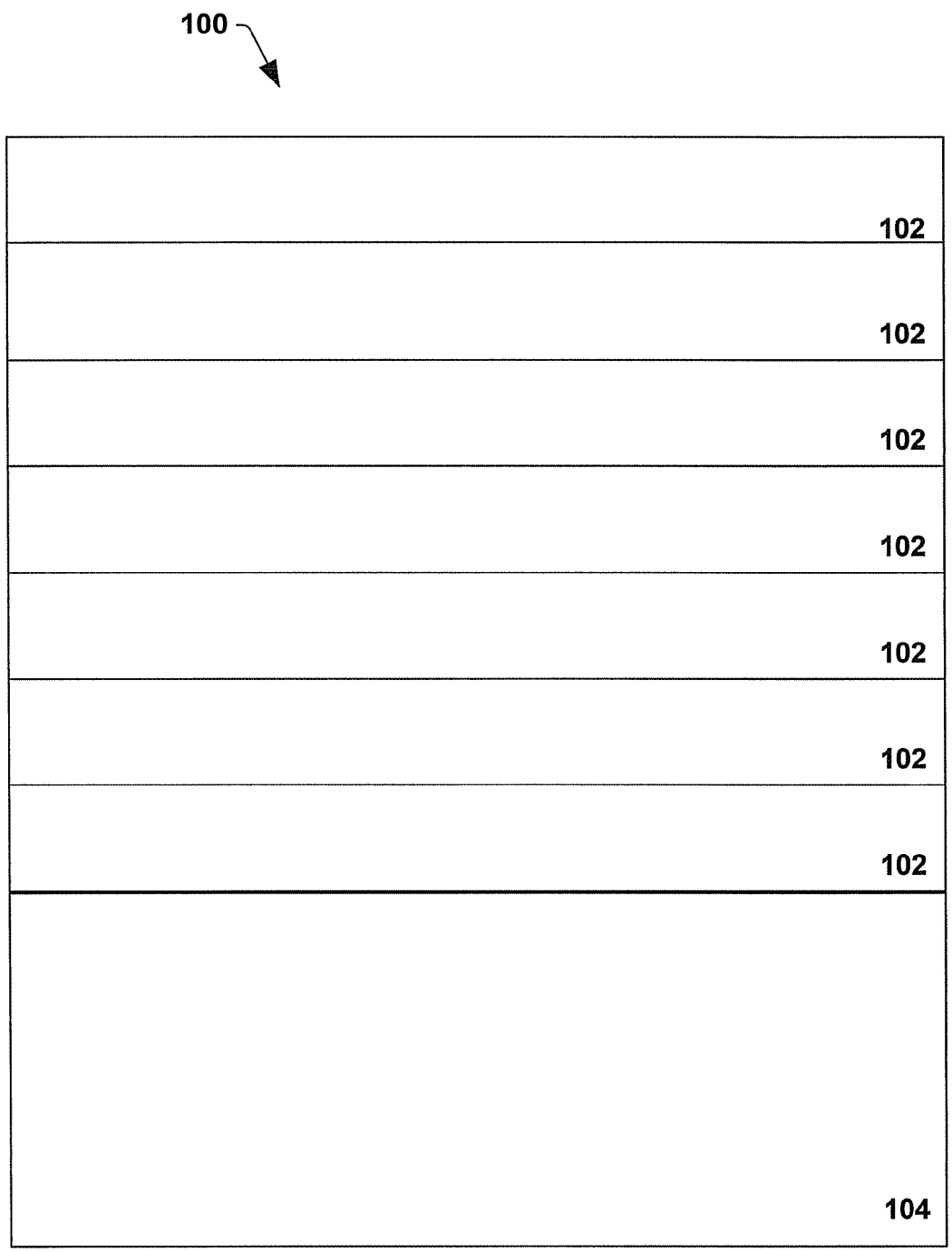
FIG. 1 is a cross sectional illustration of the sample to be measured containing the sheet material on a sensor of a thermal property measuring device in accordance with an aspect of the subject invention.

Thermal conductivity is a measure of the ability of a material to conduct heat. Thermal effusivity is a comprehensive measure for heat distribution across a given material. Thermal effusivity characterizes the thermal impedance of matter (its ability to exchange thermal energy with surroundings). Specifically, thermal effusivity is a function of the density, heat capacity, and thermal conductivity. Thermal effusivity can be calculated by taking the square root of thermal conductivity (W/mK) times the density ($kg/m^3$) times heat capacity (J/kgK). Thermal effusivity is a heat transfer property that dictates the interfacial temperature when two semi-infinite objects at different temperature touch.

The method of the subject invention can be used to determine thermal effusivity and/or thermal conductivity of a thin sheet material or of a coated substrate that has a thickness of less than about 100 µm. Since the thermal properties of sheet materials depend on the manner in which the sheet materials are made, methods that allow measurement of thermal effusivity and/or thermal conductivity of sheet material can play an important role in new product development.

The thermal effusivity and/or thermal conductivity of sheet materials can be measured by a thermal effusivity-measuring device and/or thermal conductivity-measuring device. The thermal property-measuring devices may use either a transient measurement technique or steady-state measurement technique. In the transient measurement, heat is applied to a sample over a period of time and the changing temperature response of the sample is measured. In the steady-state measurements, heat is applied to a sample until a constant temperature equilibrium is reached. There are a number of devices available to measure the thermal properties using either the transient or steady-state methods. Some of these devices may include guarded hotplate, hot wire, modified hot wire, laser flash and transient plane techniques. The subject invention can use any suitable thermal property-measuring device.

The guarded hotplate is a steady-state technique that involves placing a sample of fixed dimensions between two temperature controlled plates at different temperatures. Typically, one plate is heated while the other is cooled and the temperatures of the plates are monitored over time, until they reach constant temperatures ($\Delta T$). The steady-state temperature, sample thickness (L) and area (A) as well as the heat input (Q) to the system are used to calculate the thermal conductivity (k) from $Q = kA/L\Delta T$.

The hot wire technique is a transient method of determining thermal conductivity. The temperature rise is measured during a time interval. The method involves inserting an electrically heated wire into a sample. The heat flows out radially from the wire and the temperature of the wire is measured. The plot of these temperatures versus the logarithm of time is used to calculate thermal conductivity.

Another method of measuring thermal conductivity is the transient plane source method also called the hot disk method. This is another transient technique in which the sample surrounds a heating element, but in this case, the sensor is configured as a planar circle rather than a wire or line source. The heating of the element causes a three dimensional heat flow to occur. The interface temperature is monitored and plotted against a time function, and thermal properties are calculated from an iterative curve fit to the underlying equations.

The thermal property-measuring device may use the modified hot-wire technique. The modification to the basic hot wire design is that the heating element is supported on a backing material in the sensor and as such, the heat flows both into a sample to be measured and into the backing material.

In one embodiment, thermal effusivity and thermal conductivity can be determined using a thermal conductivity and thermal effusivity testing system under the trade designation TC-30® available from Mathis Instruments using the modified hot wire technique, operating under constant current conditions. The temperature of the heating element of the system is monitored during sample testing, and changes in the temperature at the interface between the sensor and sample surface, over the testing time, are continually measured.

The thermal properties of a sample can be measured by placing the sample on heating elements of a temperature probe/sensor of the thermal property-measuring device. A discrete quantity of electrical current is passed through the heating elements of the sensor for a discrete time. The precise quantity of electrical current and time may vary with each measurement, and can be determined by one skilled in the art. Passing the discrete quantity of electrical current through the heating elements results in a temperature rise at the sensor/sample interface and, over time, a heat flows from the sensor into the sample.

The sensor functions by measuring the temperature rise at the sensor/sample interface over time. The heat transfer properties of the sample profoundly affect the rate of this temperature rise. If the sample is a good thermal insulator, then as heating continues, very little heat is conducted away from the sensor/sample interface and the temperature at the interface rises very quickly. If the sample is a good heat conductor, then as heating continues, the heat is conducted away from the sensor/sample interface and the temperature at the interface rises very slowly.

Generally speaking, the thermal property-measuring devices have a minimum thickness requirement for measuring the thermal properties of sheet materials. For example, a thermal conductivity and thermal effusivity testing system under the trade designation TC-30® available from Mathis Instruments can determine the thermal properties of a relatively thick sheet material. The Mathis Instruments device requires that the sample sheet material have a thickness greater than 100 µm. Thus, the thermal properties of sheet materials thinner than 100 µm cannot be measured by the Mathis Instruments device.

The subject invention provides methods for determining thermal effusivity and/or thermal conductivity of sheet materials that are relatively thin, such as sheet materials having a thickness of less than about 100 µm. The subject invention also provides a method for determining thermal effusivity and/or thermal conductivity of thin coated substrates having a thickness of less than about 100 µm. In one embodiment, the thin sheet material and/or the thin coated substrate have a thickness less than about 90 µm. In another embodiment, the thin sheet material and/or the thin coated substrate have a thickness less than about 75 µm. In yet another embodiment, the thin sheet material and/or the thin coated substrate have a thickness less than about 50 µm.

The methods contain providing a sample by layering 2 or more sheet materials or coated substrates; placing the sample onto a thermal effusivity probe and/or thermal conductivity probe; and measuring thermal effusivity and/or thermal conductivity of the sample by the thermal effusivity probe and/or thermal conductivity probe.

The sample to be measured can be prepared by layering the sheet materials or coated substrates. Before the sheet materials or coated substrates are layered, the sheet materials or coated substrates may be cut into a suitable size so that the thermal property-measuring device can measure the thermal properties of the sheet materials or coated substrates. The sheet materials or coated substrates may be cut into a suitable size so that they can cover the thermal effusivity probe and/or thermal conductivity probe. In one embodiment, the sheet materials or coated substrates are cut into 100×100 mm pieces. In another embodiment, the sheet materials or coated substrates are cut into 50×80 mm pieces. In yet another embodiment, the sheet materials or coated substrates are cut into 10×70 mm pieces.

The sample contains any suitable number of pieces of sheet material or coated substrate so that the thermal property-measuring devices can measure the thermal properties of the sheet material or coated substrate. In one embodiment, the sample may be prepared by layering more than 2 sheet materials or coated substrates to ensure that the heat wave does not penetrate the sample. In another embodiment, the sample may be prepared by layering more than 3 sheet materials or coated substrates to ensure that the heat wave does not penetrate the sample. In one embodiment, the sample is provided by layering about 2 or more and about 20 or less sheet materials or coated substrates. In another embodiment, the sample is provided by layering about 3 or more and about 15 or less sheet materials or coated substrates. In yet another embodiment, the sample is provided by layering about 5 or more and about 10 or less sheet materials or coated substrates.

The sample can be prepared by simply layering the multiple sheet materials or coated substrates. The multiple sheet materials or coated substrates may be layered by binding each to the other using, for example, adhesives at the periphery of the sheet materials or coated substrates, a clip, a staple, and/or a strap.

The sheet material or coated substrate may be subject to a calendering process before layering or after layering to decrease a surface roughness of the sheet material or coated substrate. Since any air pockets in-between the sheet materials or coated substrates due to non-uniform surface roughness may have negative impact on accuracy and precision of the thermal properties measurements, calendering improves the detection accuracy and precision.

To calender the sheet materials or coated substrates, any suitable calendering devices may be employed. For example, the calendering device may have a hot calender roll surface at a temperature of about 100 degrees Celsius or more, a calender nipload that varies from about 100 to about 1,000 kN/m, and a nip width from about 0.1 to about 25 cm.

In one embodiment, by calendering the sheet materials or coated substrates having a thickness of about 40 µm or more and about 100 µm or less, the sheet materials or coated substrates have a Parker Print Surf (PPS) roughness of about 0.5 µm or more and about 5 µm or less. In another embodiment, by calendering the sheet materials or coated substrates having a thickness of about 40 µm or more and about 100 µm or less, the sheet materials or coated substrates have a PPS roughness of about 1.0 μm or more and about 3.0 μm or less. In yet another embodiment, by calendering the sheet materials or coated substrates having a thickness of about 40 μm or more and about 100 μm or less, the sheet materials or coated substrates have a PPS roughness of about 1.5 μm or more and about 2 μm or less.

The sample containing 2 or more sheet materials or coated substrates is placed onto a sample holder of the thermal property-measuring device, and the thermal properties of the sample are measured by the device. Although the orientation of the sample with respect to a probe (i.e., sensor) of the thermal property-measuring device is not crucial for obtaining useful data, the sample may be placed onto the sensor with the orientation "toward the sensor" as opposed to "away from the sensor."

For each sample, the thermal properties of the sample may be measured one or more times with optimized test times, regression start times, and cool times. In one embodiment, the thermal properties of the sample may be measured about 2 or more times and about 200 or less times. In another embodiment, the thermal properties of the sample may be measured about 30 or more times and about 150 or less times. In yet another embodiment, the thermal properties of the sample may be measured about 70 or more times and about 120 or less times.

To maximize the sheet material area or coated substrate area subject to the measurement, the bottom layer of the sample may be removed and placed on top of the sample every several measurements. In one embodiment, the bottom layer of the sample may be removed and placed on top of the sample every 6 measurements. In another embodiment, the bottom layer of the sample may be removed and placed on top of the sample every 12 measurements. In yet another embodiment, the bottom layer of the sample may be removed and placed on top of the sample every 24 measurements.

Thermal effusivity and thermal conductivity of the sample may be determined with suitable conditions. The conditions may include a testing temperature, testing size of the sample, test duration, regression start, and cooling period. In one embodiment, the thermal effusivity and thermal conductivity of the sheet material or coated substrate may be measured with the following conditions: testing temperature, about 18 to 40 degrees Celsius; testing size of the sample, about 100× 100 mm; test duration, from about 0.25 seconds to about 5 minutes; regression start, from about 0.1 second to about 3 minutes; cooling period, from about 1 to about 20 minutes. In another embodiment, the thermal effusivity and thermal conductivity of the sheet material or coated substrate may be measured with the following conditions: testing temperature, about 20 to 35 degrees Celsius; testing size of the sample, about 50×80 mm; test duration, from about 0.5 seconds to about 2 minutes; regression start, from about 0.25 seconds to about 20 seconds; cooling period, from about 2 to about 5 minutes. In yet another embodiment, the thermal effusivity and thermal conductivity of the sheet material or coated substrate may be measured with the following conditions: testing temperature, about 23 to 27 degrees Celsius; testing size of the sample, about 10×70 mm; test duration, from about 1 second to about 30 seconds; regression start, from about 0.5 seconds to about 10 seconds; cooling period, from about 2 to about 4 minutes.

Thermal effusivity and thermal conductivity values of the sheet materials and coated substrates can vary depending on many parameters, including the nature of the sheet material and coated substrate, the formulation of the sheet material and coated substrate, temperature and humidity during measurement, calendering conditions, smoothness of the sheet material and coated substrate, instrument calibration, etc. Thus, it may be suitable to measure and evaluate the thermal properties of the sheet materials and coated substrates on a comparative basis (i.e., comparing to control that is measured under the same conditions as the rest of the samples) rather than by using their absolute measured thermal property values. Any differences greater than the standard deviation of respective measurements, typically about 0.5% to about 1%, may be considered real.

The sheet material or coated substrate is generally in sheet form. That is, the sheet material or coated substrate is in the form of pages, webs, ribbons, tapes, belts, films, cards and the like. Sheet form indicates that the sheet material or coated substrate has two large surface dimensions and a comparatively small thickness dimension. The coated substrate may comprise at least one substrate layer and at least one coat layer.

The sheet material or coated substrate can be any of opaque, transparent, translucent, colored, and non-colored (white). Examples of sheet materials and substrate layer materials include paper, filamentous synthetic materials, and synthetic films such as cellophane and synthetic polymeric sheets (the synthetic films can be cast, extruded, or otherwise formed). In this sense, the chemical composition of the sheet material or coated substrate is not critical in the subject invention.

The coated substrate has at least a substrate layer and a coat layer. In one embodiment, the coated substrate may be thermal paper or intermediate product of the thermal paper. The thermal paper typically may have at least three layers: a substrate layer, an active layer for forming an image, and a coat layer between the substrate layer and active layer. The intermediate product of the thermal paper may have a substrate layer and a coat layer on the substrate layer. The coat layer can be made so that it possesses a thermal conductivity and thermal effusivity that improve the quality and/or efficiency of thermal paper printing. The active layer subsequently develops an image by the application of heat. When passing through an imaging device, precise measures of heat applied by a printhead cause a reaction that creates an image (typically black or color) on the thermal paper. Thermal paper may optionally have one or more additional layers including a top coating layer (sometimes referred to as a protective layer) over the active layer, a backside barrier adjacent the substrate layer, image enhancing layers, or any other suitable layer to enhance performance and/or handling.

When the coated substrate is a thermal paper or intermediate product of the thermal paper, the substrate layer is of sufficient thickness to support at least an active layer and coat layer, and optionally of sufficient thickness to further support additional, optional layers such as a top coating layer and/or a backside barrier. In one embodiment, the substrate layer has a basis weight of about 20 $g/m^2$ or more and about 100 $g/m^2$ or less. In another embodiment, the substrate layer has a thickness of about 10 μm or more and about 100 μm or less. In yet another embodiment, the substrate layer has a thickness of about 20 μm or more and about 80 μm or less. In still yet another embodiment, the substrate layer has a thickness of about 30 μm or more and about 70 μm or less.

The coat layer may contain a binder and a porosity improver and has a desirable thermal effusivity and thermal conductivity. The coat layer may further and optionally contain a dispersant, wetting agent, and other additives, so long as the thermal effusivity values are maintained. In one embodiment, the coat layer does not contain image forming components; that is, the coat layer does not contain any of a dye, chromogenic material, and/or organic and inorganic pigments.

The coat layer contains a sufficient amount of binder to hold the porosity improver. In one embodiment, the coat layer contains about 20% by weight or more and about 95% by weight or less of binder.

Examples of binders include water-soluble binders such as starches, hydroxyethyl cellulose, methyl cellulose, carboxymethyl cellulose, gelatin, casein, polyvinyl alcohol, modified polyvinyl alcohol, sodium polyacrylate, acrylic amide/acrylic ester copolymer, acrylic amide/acrylic ester/methacrylic acid terpolymer, alkali salts of styrene/maleic anhydride copolymer, alkali salts of ethylene/maleic anhydride copolymer, polyvinyl acetate, polyurethane, polyacrylic esters, styrene/butadiene copolymer, acrylonitrile/butadiene copolymer, methyl acrylate/butadiene copolymer, ethylene/vinyl acetate copolymer, and the like. Further examples of binders include polyester resin, vinyl chloride resin, polyurethane resin, vinyl chloride-vinyl acetate copolymer, vinyl chlorideacrylonitrile copolymer, epoxy resin, nitrocellulose, and the like.

The porosity improver of the subject invention has at least one of high surface area, high pore volume, narrow particle size distribution, and/or high porosity when assembled in a layer (and thus appear to possess a high pore volume). Examples of the porosity improver include one or more of calcined clays such as calcined kaolin, flash calcined kaolin, and calcined bentonite, acid treated bentonite, high surface area alumina, hydrated alumina, silica, silica gel, high silica zeolite (high silica to alumina mole ratio, such as at least about 3:1 or at least about 10:1), microporous particles, alumina phosphates, metal alumina phosphates, and the like. These compounds are commercially available through a number of sources.

The coat layer may contain at least one porosity improver, at least two porosity improvers, at least three porosity improvers, and so on. For the porosity improvers other than calcined clays, the porosity improver of the subject invention has one or more of at least about 60% by weight of the particles have a size of 2 μm or less, a surface area of at least about 5 m$^2$/g, and a pore volume of at least about 0.1 cc/g. In one embodiment, when the porosity improvers are calcined clay, the calcined clay has one or more of at least about 60% by weight of the particles have a size of 2 μm or less, at least about 40% by weight of the particles have a size of 1 micron or less, a surface area of at least about 5 m$^2$/g, and a pore volume of at least about 0.1 cc/g. The non-calcined clay porosity improver or the calcined clay porosity improver may have a pore volume of at least about 0.1 cc/g.

Examples of commercially available calcined clay include those under the trade designations such as Ansilex® 93, Satintone®, and Translink®, available from BASF Catalysts LLC of Iselin, N.J.

The coat layer contains a sufficient amount of a porosity improver to contribute to providing thermal insulating properties, such as a beneficial thermal effusivity, that facilitate high quality image formation in the active layer. In one embodiment, the coat layer contains about 5% by weight or more and about 80% by weight or less of a porosity improver.

When the coated substrate is a thermal paper or an intermediate product of the thermal paper, the coat layer may have a sufficient thickness to provide thermal insulating properties, such as a beneficial thermal effusivity and thermal conductivity, which facilitate high quality image formation in the active layer. In one embodiment, the coat layer has a thickness of about 0.5 μm or more and about 20 μm or less.

Another beneficial aspect of the coat layer is the thickness uniformity achieved when formed across the substrate layer. In this connection, the thickness of the coat layer does not vary by more than about 10 μm when selecting two random locations of the coat layer for determining thickness.

When the coated substrate is a thermal paper or intermediate product of the thermal paper, the coated substrate may contain an active layer containing image forming components that become visible to the human eye or a machine reader after exposure to localized heat. The active layer contains one or more of a dye, chromogenic material, developer, inert pigment, antioxidants, lubricants, polymeric binder, sensitizer, stabilizer, wetting agents, and waxes. The active layer is sometimes referred to as a reactive layer. The components of the active layer are typically uniformly distributed throughout the active layer. Examples of dyes, chromogenic materials, and inert pigments include fluorescent, organic and inorganic pigments. These compounds may lead to black-white printing or color printing. Examples of developers include acidic developers such as acidic phenolic compounds and aromatic carboxylic acids. Examples of sensitizers include ether compounds such as aromatic ether compounds. One or more of any of the active layer components may or may not be microencapsulated.

The active layer has a sufficient thickness to provide a visible, detectable and/or desirable image on the thermal paper for an end user. In one embodiment, the active layer has a thickness of about 1 μm or more and about 20 μm or less.

The subject invention can be further understood in connection with the drawings. Referring to FIG. 1, a cross sectional view of a sample 100 containing seven sheet materials 102 on a sensor 104 of a thermal property-measuring device is shown. The sheet material 102 has a size of 10×70 mm. The sample 100 is prepared by layering seven sheet materials 102. The sample 100 is placed onto the sensor 104 of the thermal property-measuring device. Approximately 100 measurements are performed at about 30 degrees Celsius with, for example, 1 second test duration, 0.2 seconds regression start and 3 minutes cooling time. The bottom sheet material of the sample may be removed and placed on top of the sample every 12 measurements.

Figure 2:
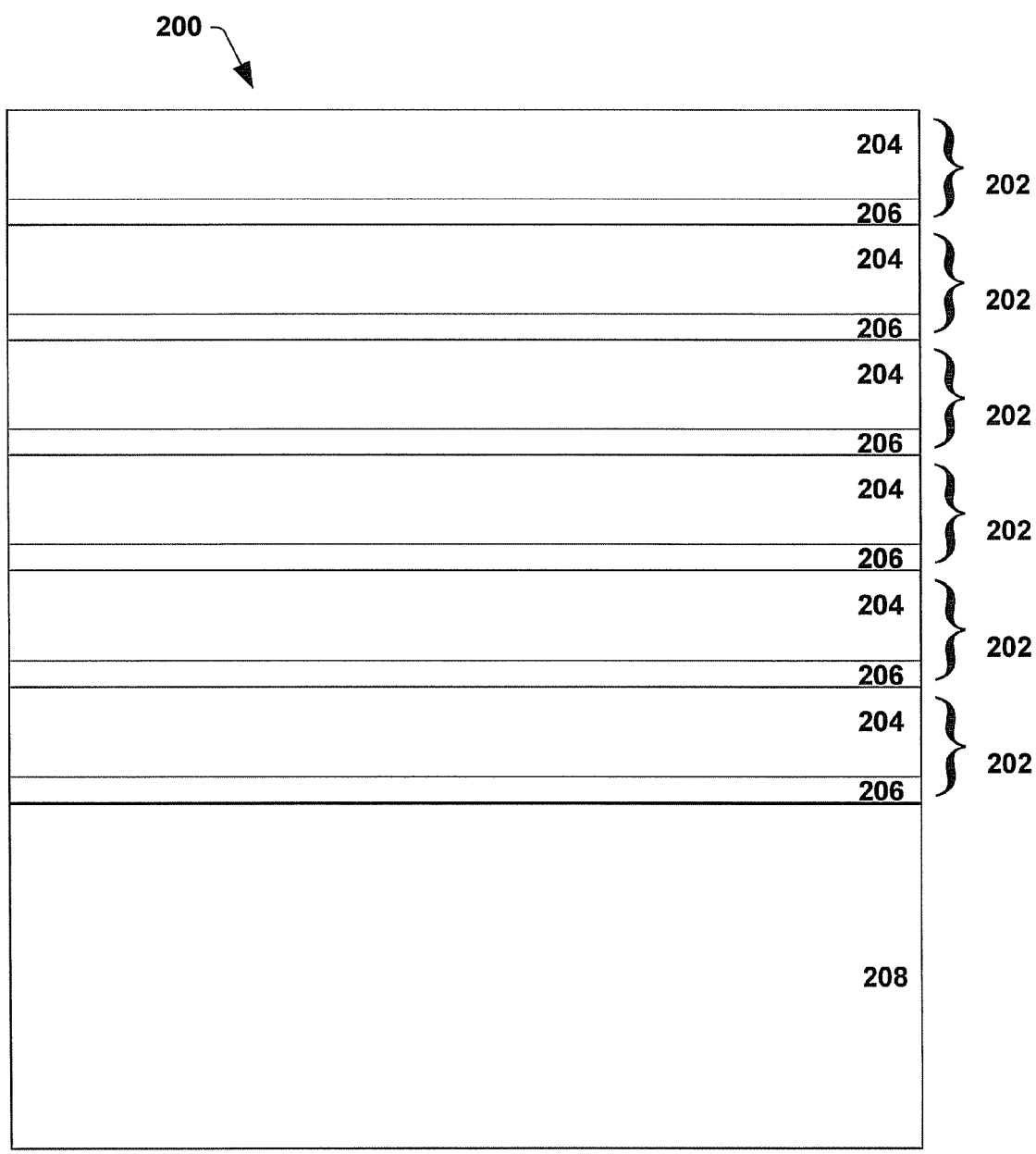
FIG. 2 is a cross sectional illustration of the sample to be measured containing the coated substrate on a sensor of a thermal property measuring device in accordance with another aspect of the subject invention.

Referring to FIG. 2, a cross sectional view of a sample 200 containing six coated substrates 202 on a sensor 208 of a thermal property-measuring device is shown. The coated substrate 202 contains a substrate layer 204 and a coat layer 206. When the coated substrate is a thermal paper or an intermediate product of the thermal paper, the substrate layer 204 typically contains a sheet of paper. On one side (the writing side or image side of the thermal paper) of the substrate layer 204 is a coat layer 206. Although not shown in the figures, the coated substrate may contain additional layers, such as an active layer on the coat layer 206. The coat layer 206 contains a porosity improver in a binder and provides thermal insulating properties and slows the transfer of thermal energy emanating from a thermal print head to the substrate layer 204 during the writing or imaging process.

The coated substrate 202 has a size of 30×80 mm. The coated substrate 202 may be calendered to a PPS roughness of about 1 μm or more and about 4 μm or less before measuring the thermal properties. The sample 200 is prepared by layering six coated substrates 202. The thickness of the coated substrate is about 60 μm or more and about 90 μm or less. The sample 200 is placed onto the sensor 208 of the thermal property-measuring device, for example Mathis Instruments TC-30®. Approximately 120 measurements are performed at about 25 degrees Celsius with, for example, 1.5 seconds test duration, 0.9 seconds regression start and 2 minutes cooling time. The bottom sheet material of the sample may be removed and placed on top of the sample every 12 measurements.

While the invention has been explained in relation to certain embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A method for determining thermal effusivity and/or thermal conductivity of a sheet material having a thickness of less than about 100 μm, comprising:
   providing a sample by layering 2 or more sheet materials;
   placing the sample in direct contact onto a thermal effusivity probe and/or thermal conductivity probe; and
   measuring thermal effusivity and/or thermal conductivity of the sample by the thermal effusivity probe and/or thermal conductivity probe.

2. The method of claim 1, wherein the sheet material comprising at least one substrate layer and at least one coat layer.

3. The method of claim 1, wherein the sample is provided by layering 2 or more and about 20 or less sheet materials.

4. The method of claim 1, wherein the sample is provided by layering 3 or more and about 15 or less sheet materials.

5. The method of claim 1, wherein the sample is provided by layering 5 or more and about 10 or less sheet materials.

6. The method of claim 1, further comprising calendering the sheet material.

7. The method of claim 1, wherein after measuring thermal effusivity and/or thermal conductivity of the sample, the bottom sheet material of the sample is removed and layered on top of the sample and thermal effusivity and/or thermal conductivity of the sample is re-measured by the thermal effusivity probe and/or thermal conductivity probe.

8. A method for determining thermal effusivity and/or thermal conductivity of a coated substrate having a thickness of less than about 100 μm, comprising:
   providing a sample by layering 2 or more coated substrates;
   placing the sample in direct contact onto a thermal effusivity probe and/or thermal conductivity probe; and
   measuring thermal effusivity and/or thermal conductivity of the sample by the thermal effusivity probe and/or thermal conductivity probe.

9. The method of claim 8, wherein the coated substrate comprising at least one substrate layer and at least one coat layer.

10. The method of claim 8, wherein the sample is provided by layering 2 or more and about 20 or less coated substrates.

11. The method of claim 8, wherein the sample is provided by layering 3 or more and about 15 or less coated substrates.

12. The method of claim 8, wherein the sample is provided by layering 5 or more and about 10 or less coated substrates.

13. The method of claim 8, further comprising calendering the coated substrate.

14. The method of claim 8, wherein after measuring thermal effusivity and/or thermal conductivity of the sample, the bottom coated substrate of the sample is removed and layered on top of the sample and thermal effusivity and/or thermal conductivity of the sample is re-measured by the thermal effusivity probe and/or thermal conductivity probe.

15. The method of claim 8, wherein the coated substrate has a Parker Print Surf roughness of about 0.5 μm or more and about 5 μm or less.

16. The method of claim 9, wherein the coat layer comprising at least one binder and at least one porosity improver.

17. The method of claim 9, wherein the substrate layer has a thickness of about 10 μm or more and about 100 μm or less and the coat layer has a thickness of about 0.5 μm or more and about 20 μm or less.

18. A method for determining thermal effusivity and/or thermal conductivity of a coated substrate having a thickness of less than about 100 μm, comprising:
   providing the coated substrate, the coated substrate comprising at least one substrate layer and at least one coat layer, the coat layer comprising about 20% by weight or more and about 95% by weight or less of at least one binder and about 5% or more and about 80% or less of at least one porosity improver;
   providing a sample by layering 2 or more coated substrates;
   placing the sample in direct contact onto a thermal effusivity probe and/or thermal conductivity probe; and
   measuring thermal effusivity and/or thermal conductivity of the sample by the thermal effusivity probe and/or thermal conductivity probe.

19. The method of claim 18, wherein the sample is provided by layering 3 or more and about 15 or less coated substrates.

20. The method of claim 18, wherein the coated substrate has a Parker Print Surf roughness of about 0.5 μm or more and about 5 μm or less.

* * * * *